United States Patent [19]

Watanabe et al.

[11] Patent Number: 5,118,863
[45] Date of Patent: Jun. 2, 1992

[54] PROCESS FOR PRODUCING AN α,β-UNSATURATED CARBONYL COMPOUND

[75] Inventors: Kiyoshi Watanabe; Rikitaro Matsuoka, both of Yokohama, Japan

[73] Assignee: Nippon Zeon Co., Ltd., Tokyo, Japan

[21] Appl. No.: 758,995

[22] Filed: Sep. 5, 1991

Related U.S. Application Data

[63] Continuation-in-part of Ser. No. 610,644, Nov. 8, 1990, abandoned, and a continuation-in-part of Ser. No. 537,860, Jun. 14, 1990, abandoned.

[30] Foreign Application Priority Data

Jun. 22, 1989 [JP]  Japan .................. 1-160428
Nov. 11, 1989 [JP]  Japan .................. 1-293697

[51] Int. Cl.⁵ ............................................ C07C 45/48
[52] U.S. Cl. ................................ 568/356; 568/398; 568/319
[58] Field of Search ................. 568/356, 319, 398

[56] References Cited

U.S. PATENT DOCUMENTS 4,575,570  3/1986  Kataoka et al. .................. 568/356

FOREIGN PATENT DOCUMENTS 59-73536  4/1984  Japan .
60-32745  2/1985  Japan .
60-36435  2/1985  Japan .
60-45544  3/1985  Japan .

OTHER PUBLICATIONS

Patent Abstracts of Japan, vol. 9, No. 153, p. 110, Kokai-No. 60-32742 (1985).
Patent Abstracts of Japan, vol. 9, No. 45, p. 14, Kokai-No. 59-186938 (1985).
Chemistry Letters, pp. 1133-1136 (1984).
Chemistry Letters, pp. 1721-1724 (1984).
Tetrahedron, vol. 42, No. 11, pp. 2971-2977 (1986).
Tetrahedron, vol. 22, No. 37, pp. 3591-3594 (1981).
Minami et al., Synthesis, vol. 2, No. 11, pp. 992-998 (1987).

Primary Examiner—James H. Reamer
Attorney, Agent, or Firm—Armstrong, Nikaido, Marmelstein, Kubovcik & Murray

[57] ABSTRACT

A process for producing an α,β-unsaturated carbonyl compound represented by formula (II):

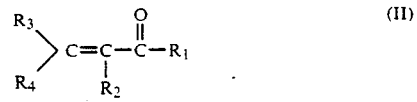

which includes subjecting an alkenyl ester represented by formula (I):

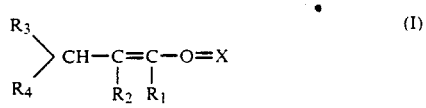

and an allyl type carbonic ester to catalytic reaction in the presence of a platinum group metal compound catalyst without the necessity of an organotin alkoxide. The subsequent addition of a phosphorus-containing compound, followed by heating, results in the decomposition and removal of unreacted allyl type carbonic ester and reaction by-product.

51 Claims, No Drawings

PROCESS FOR PRODUCING AN α,β-UNSATURATED CARBONYL COMPOUND

This is a continuation-in-part application of U.S. Ser. No. 07/610,644 filed on Nov. 8, 1990, now abandoned, and U.S. Ser. No. 07/537,860, filed on Jun. 14, 1990 and now abandoned.

BACKGROUND OF THE INVENTION

This invention relates to a process for producing an α,β-unsaturated carbonyl compound. More particularly, it relates to a process for producing an α,β-unsaturated carbonyl compound useful for production of chemical substances such as medicines, agricultural chemicals, perfumes, etc., by the reaction of an alkenyl ester and an allyl type carbonic ester. The invention is also directed to purification of such an α,β-unsaturated compound.

α,β-unsaturated carbonyl compounds such as 2-cyclopentenone, 2-cyclohexenone, 2-cyclododecenone, etc. are very useful chemical substances in the fields of medicines, agricultural chemicals, perfumes, etc.

As a process for synthesizing such an unsaturated carbonyl compound, there has been reported a process which comprises treating an alkenyl ester and an allyl type carbonic ester with a platinum group metal compound catalyst in the presence of an organotin alkoxide (Jap. Pat. Appln. Kokai (Laid-Open) No. 60-36435, and Chemistry Letters 1133–1136 (1984)). However, the organotin alkoxide used as indispensable component in this process is difficult to handle and it is insufficient in safety from the viewpoint of industrial hygiene and contamination of the organotin alkoxide to a final product.

As a process for producing such an α,β-unsaturated carbonyl compound, there has been known, for example, a process which comprises reacting, as illustrated by the formula shown below, an alkenyl ester such as 1-cyclopentenyl acetate with an allyl type carbonic ester such as allyl methyl carbonate in the presence of a platinum group metal compound catalyst.

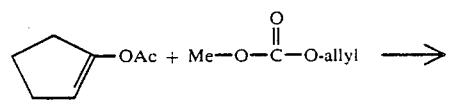

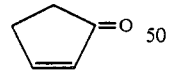

This process uses easily available compounds as starting materials and permits relatively efficient production of an α,β-unsaturated carbonyl compound. However, it requires selective separation and purification of the reaction product, i.e., the α,β-unsaturated carbonyl compound because the actual reaction mixture contains unreacted allyl type carbonic ester and an allyl acetate by-product in addition to the α,β-unsaturated carbonyl compound.

For reducing the amount of the residual starting allyl type carbonic ester in the reaction mixture, reduction of the amount of the allyl type carbonic ester used may be considered. However, reduction of the allyl type carbonic ester is substantially impossible because for producing the α,β-unsaturated carbonyl compound, it is essential to use an amount of the allyl type carbonic ester which is equivalent to or larger than the amount of the alkenyl ester. Therefore, the presence of unreacted allyl type carbonic ester in the reaction mixture is unavoidable.

On the other hand, as a method for the separation and purification of the α,β-unsaturated carbonyl compound from the reaction mixture, purification by distillation may be considered at first. However, when the boiling point of the unreacted, residual allyl type carbonic ester is close to that of the desired product, i.e., the α,β-unsaturated carbonyl compound, they cannot be separated from each other by distillation. Therefore, a method is required by which the α,β-unsaturated carbonyl compound can be separated efficiently in high purity by a means other than distillation.

As information concerning a method for this separation, it has been reported that allyl carbonate can be decomposed by reacting triphenylphosphine and palladium acetate with allyl carbonate in the molar ratio of triphenylphosphine/palladium acetate=5 with heating [Tetrahedron Letters, 12, 3591 (1981)]. However, close investigation by the present inventors proved that allyl acetate by-product could not be decomposed by such a method.

In addition, the by-product allyl acetate can be decomposed by hydrolysis with a strong acid or a strong alkali or by heating at a high temperature, but when such a decomposition method is applied to a reaction system for producing the α,β-unsaturated carbonyl compound, decomposition of the desired α,β-unsaturated carbonyl compound is inavoidable.

Accordingly, it has been very difficult to separate and purify the α,β-unsaturated carbonyl compound efficiently in high purity from the reaction mixture obtained by the reaction of the alkenyl ester with the allyl type carbonic ester, by a heretofore known method.

BRIEF SUMMARY OF THE INVENTION

An object of the present invention is to overcome the defects in the prior art and to provide a novel process for producing an α,β-unsaturated carbonyl compound which makes it possible to obtain the α,β-unsaturated carbonyl compound efficiently in high purity from a reaction mixture.

In one aspect, the present invention relates to a process for producing an α,β-unsaturated carbonyl compound represented by formula (II):

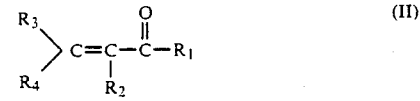

wherein $R_1$, $R_2$, $R_3$ and $R_4$ are independently hydrogen atoms or hydrocarbon residues, and $R_1$, $R_2$, $R_3$ and $R_4$ may be linear or may form one or more rings when taken together in arbitrary combinations, which comprises subjecting an alkenyl ester represented by formula (I):

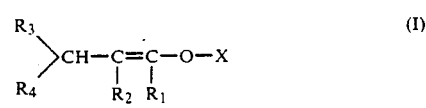

wherein $R_1$, $R_2$, $R_3$ and $R_4$ have the same meanings as those defined above, and X is an acyl group, and an allyl type carbonic ester to catalytic reaction in the presence of a platinum group metal compound catalyst. In a second aspect, the invention includes a subsequent step of adding a phosphorus-containing compound, followed by heating.

DETAILED DESCRIPTION OF PREFERRED EMBODIMENTS

Easily available compounds can be used as starting materials in the process of the present invention, as in conventional processes. As the starting alkenyl ester, there is used a compound of formula (I):

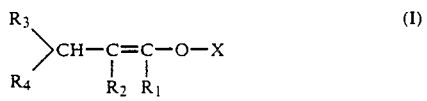

(I)

In formula (I), $R_1$, $R_2$, $R_3$ and $R_4$ are independently hydrogen atoms or hydrocarbon residues. As the hydrocarbon residues, there can be exemplified by alkyl groups such as methyl, ethyl, propyl and pentyl; an aryl group, such as a phenyl group; and a trityl group. $R_1$, $R_2$, $R_3$ and $R_4$ may be taken together in arbitrary combinations to form one or more rings. For example, $R_1$ may be bonded to $R_2$, $R_3$ or $R_4$ to form a ring such as a cyclopentane, cyclopentene, cyclohexane, cyclohexene, cyclododecane, cyclododecene ring or the like. X in formula (I) is an acyl group.

Specific examples of the alkenyl ester of the formula (I) described above include 1-cyclopentenyl acetate, 1-cyclohexenyl acetate, 6-methyl-1-cyclopentenyl acetate, 6-methyl-1-cyclohexenyl acetate, 6-ethyl-1-cyclopentenyl acetate, 6-ethyl-1-cyclohexenyl acetate, 1-cycloheptenyl acetate, 1-cyclododecenyl acetate, 1-cyclopentenyl propionate, 1-cyclohexenyl propionate, 1-cyclopentenyl butyrate, 1-cyclohexenyl butyrate, 1-cyclopentenyl benzoate, 1-cyclohexenyl benzoate, 1-phenyl-1-butenyl acetate, 1-propenyl acetate, 1-hexenyl acetate, 3-methyl-1-butenyl acetate, 3-methyl-1-propenyl acetate, and 3-phenyl-1-propenyl acetate. Of these, cycloalkenyl esters are preferable. In particular, cycloalkenyl esters having a 5- to 7-membered ring or a 12-membered ring are preferable. As the alkenyl esters exemplified above, those synthesized by conventional methods can be used. For example, 1-cyclopentenyl acetate can easily be obtained by reacting cyclopentanone with isopropenyl acetate in the presence of an acid or by reacting cyclopentanone with acetic anhydride.

The allyl type carbonic ester, i.e., another starting material in the production process of the present invention, is an carbonic ester having at least one allyl or its allied residue and can be represented by formula (III):

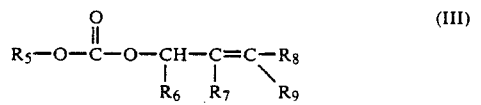

(III)

wherein $R_5$ is a hydrocarbon residue, and $R_6$, $R_7$, $R_8$ and $R_9$ are independently hydrogen atoms or hydrocarbon residues.

The hydrocarbon residues include, for example, alkyl groups having 1 to 8 carbon atoms (e.g. methyl, ethyl group, etc.) and alkenyl groups having 2 to 8 carbon atoms. Specific examples of such an allyl type carbonic ester are allyl methyl carbonate, allyl ethyl carbonate, allyl propyl carbonate, allyl butyl carbonate, allyl pentyl carbonate, crotyl methyl carbonate, ethyl methallyl carbonate, and diallyl carbonate. Allyl esters, crotyl esters and methallyl esters, in which $R_5$ is a lower alkyl group having 4 or less carbon atoms, are preferred.

As to the proportions of the amount of alkenyl ester and the allyl type carbonic ester, the allyl type carbonic ester is usually used in an amount of 0.8 to 5 moles, preferably 1 to 3 moles, per mole of the alkenyl ester.

In the reaction of the alkenyl ester with the allyl type carbonic ester, a platinum group metal compound catalyst is used. As the platinum group metal compound catalyst, there may be used either a platinum metal compound per se or a catalyst composed of a platinum group metal compound and a ligand.

As the platinum group metal compound, there can be used, for example, various inorganic acid salts, organic acid salts or complexes of palladium, platinum, rhodium, iridium or ruthenium. More specific examples thereof are tris(dibenzylideneacetone) dipalladium (0),tris(tribenzylideneacetylacetone)tripalladium (0), palladium acetate, palladium propionate, palladium butyrate, palladium benzoate, palladium acetylacetonate, palladium nitrate, palladium sulfate, palladium chloride, platinum [II] acetate, and platinum acetylacetonate. These platinum group metal compounds may be used singly or in combination of two or more thereof.

Palladium is particularly preferable as platinum group metal element from the viewpoint of reactivity. Zero-valent olefin complexes or divalent organic compounds are also preferred examples of the platinum group metal compound.

In the case where an inorganic strong acid salt is used as the platinum group metal compound catalyst, it is preferable to place together therewith potassium acetate, sodium alkoxides, tertiary amines or the like.

Monodenate or multidentate electron donor compounds having an element of Group V of the periodic table, i.e., nitrogen, phosphorus, arsenic or antimony, can be used as the ligand.

Specific examples of the ligand are nitrogen-containing compounds such as pyridine, quinoline, trimethylamine, triethylamine, tributylamine, $\alpha,\alpha'$-dipyridine, 1,10-phenanthroline and N,N,N,'N'-tetramethylethylenediamine; phosphorus-containing compounds such as triethylphosphine, tri-n-butylphosphine, tri-n-dodecylphosphine, triphenylphosphine, tri-o-tolylphosphine, tri-p-biphenylphosphine, tri-o-methoxyphenylphosphine, phenyldiphenoxyphosphine, triethyl phosphite, tri-n-butyl phosphite, tri-n-hexyl phosphite, triphenyl phosphite, tri-o-tolyl phosphite, triphenyl thiophosphite, $\alpha,\beta$-ethylenedi(diphenyl) phosphine, $\alpha,\beta$-ethylenedi(dibutyl)phosphine and $\alpha,\tau$-propylenedi(diphenyl)phosphine; arsenic-containing compounds such as triethylarsine, tributylarsine and triphenylarsine; and antimony-containing compounds such as tripropylstibine triphenylstibine. Of these, the nitrogen-containing compounds and the phosphorus-containing compounds are preferable from the viewpoint of activity, selectivity and economical benefit of reaction.

Such a ligand is, of course, not always indispensable as a catalyst constituent. However, catalyst stability can be greatly improved by using the ligand in a properly adjusted amount. The amount of the ligand used is usually 2.5 moles or less, preferably about 0.1 to about 2 moles, per mole of the platinum group metal compound.

When the ligand is used, the platinum group metal compound and the ligand may be previously reacted with each other, or they may be added to a reaction system separately to prepare the catalyst in the reaction system.

The amount of the platinum group metal compound catalyst used is properly determined depending on the kinds of the alkenyl ester and the catalyst. It is usually in such a proportion that the amount of the platinum group metal compound is 0.01 to 10 moles, preferably 0.1 to 5 moles, per 100 moles of the alkenyl ester.

The reaction of the present is carried out by heating the above two starting materials in the presence of the catalyst. For example, a reaction equation in the case of using 1-cyclopentenyl acetate and allyl methyl carbonate is as follows:

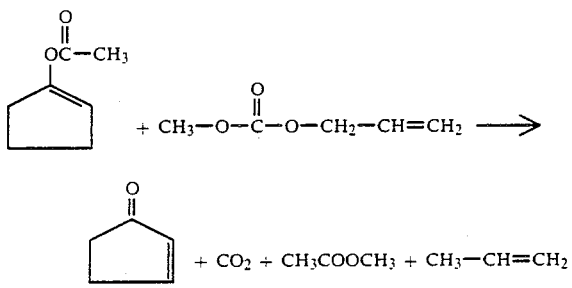

The reaction temperature is usually 50° C. or higher, preferably 55° C. to 150° C., and the reaction time is usually 10 minutes to 20 hours.

A diluent can improve the activity and selectivity of the reaction and the stability of the catalyst. Illustrative diluents include nitriles such as acetonitrile, propionitrile, and benzonitrile; sulfoxides such as dimethyl sulfoxide and diethyl sulfoxide; amides such as dimethylformamide, diethyl-formamide, dimethylacetamide, dimethylpropioamide, and N-methylpyrrolidone; ethers such as tetrahydrofuran, dioxane, dibutyl ether, and ethylene glycol dimethyl ethers; ketones such as acetone, methyl ethyl ketone, methyl isobutyl ketone, and cyclohexanone; esters such as methyl acetate, ethyl acetate, propyl acetate, and ethyl propionate; alcohols such as ethanol, propanol, tert-butanol, ethylene glycol, diethylene glycol and diethylene glycol monoethyl ether; alkanes such as n-hexane, and cyclohexane; and aromatic hydrocarbons such as benzene, toluene, and xylene. Of these, the aprotic polar solvents, in particular, the nitriles, the amides, the ethers, the ketones and the esters are preferred.

The amount of the diluent used depends on the kinds of starting materials and the catalyst, etc. Usually, the diluent is used preferably in such a proportion that the total concentration of the alkenyl ester and the allyl type carbonic ester becomes 1 to 50% by weight.

After completion of the reaction, a desired product is separated from the reaction mixture by a conventional method, whereby there can be obtained an $\alpha,\beta$-unsaturated carbonyl compound (i.e., an $\alpha,\beta$-unsaturated ketone or an $\alpha,\beta$-unsaturated aldehyde) of high purity. Such an unsaturated carbonyl compound is suitable as an intermediate for synthesis of various useful compounds, in particular, as an intermediate for perfumes, medicines, etc.

The present invention is more specifically illustrated with the following examples.

EXAMPLE 1

Into a reactor were charged 0.1 mole of 1-cyclopentenyl acetate, 0.12 mole of allyl methyl carbonate and 50 ml of acetonitrile, and the mixture heated up to the boiling point of the solvent with stirring; and 0.001 mole of palladium acetate was added. Then, the reaction was carried out with refluxing under nitrogen for 2 hours. The reaction mixture was analyzed by gas chromatography to find that 2-cyclopenten-1-one (hereinafter abbreviated to CPE) had been produced in 93% yield. Such a compound was identified by IR, NMR and MS spectroscopy.

EXAMPLE 2

Reaction was carried out in the same manner as in Example 1, except for adding 0.001 mole of triphenylphosphine in addition to palladium acetate. Consequently, the yield of CPE was 94%.

EXAMPLE 3

Reaction was carried out in the same manner as in Example 1, except for using 0.001 mole of tris(dibenzylideneacetone) dipalladium (0) in place of palladium acetate. Consequently, the yield of CPE was 92%.

EXAMPLE 4

Reaction was carried out according to Example 1, except for using 50 ml of dimethyl sulfoxide in place of acetonitrile. Consequently, the yield of CPE was 93%.

EXAMPLE 5

Reaction was carried out according to Example 4, except for using 1-cyclohexenyl acetate as a starting material. Consequently, 2-cyclohexene-1-one was obtained in 42% yield.

EXAMPLE 6

Reaction was carried out according to Example 4, except for using 4-heptenyl acetate as a starting material. Consequently, 2-heptene-4-one was obtained in 26% yield.

In a second embodiment the process of the present invention is further characterized in that after the reaction is carried out in the manner described above, a phosphorus-containing compound is added to the reaction mixture followed by heating. The unreacted allyl type carbonic ester and the by-product which remain in the reaction mixture can be decomposed and removed at the same time by the addition of a phosphorus-containing compound followed by heating. Accordingly, a desired $\alpha,\beta$-unsaturated carbonyl compound alone can easily be separated and purified.

As the phosphorus-containing compound added in this case, there can be used, for example, the phosphorus-containing compounds exemplified as the ligand of the above-mentioned platinum group metal compound catalyst.

As to the amount of the phosphorus-containing compounded added, the total amount of the phosphorus-containing compound used in the previous catalytic reaction and the subsequent reaction with heating is preferably such that the molar ratio of the phosphorus-containing compound to the platinum group metal compound is at least 3:1. When the phosphorus-containing compound is added in such an amount, not only the unreacted allyl type carbonic ester but also the by-product can be completely decomposed and removed.

When the phosphorus-containing compound is present as the ligand of the catalyst in the previous catalytic reaction, the total molar ratio of the phosphorus-containing compound to the platinum group metal compound is adjusted by adjusting the amount of the phosphorus-containing compound added in the subsequent reaction with heating. The phosphorus-containing compound may be used in an amount of much larger than 3 moles per mole of the platinum group metal compound, but too large an amount thereof is not economical and therefore the amount thereof is preferably 10 moles or less. However, when the phosphorus-containing compound is used in an amount of 2 moles or more in the previous catalytic reaction, the reaction does not proceed depending on the kinds of the starting materials, and hence care should be taken.

Reaction condition:
Temperature: usually 50° C. higher, preferably 55° C. to 150° C.
Time: 30 minutes to 10 hours Since the unreacted starting compound and the by-product are effectively decomposed by the reaction with heating described above, a desired $\alpha,\beta$-unsaturated carbonyl compound can be separated and purified efficiently in high purity by distillation.

This embodiment of the present invention is more specifically illustrated with the following examples.

EXAMPLE 7

20 mmole of 1-cyclopentenyl acetate and 24 mmoles of allyl methyl carbonate were subjected to catalytic reaction in the presence of 0.2 mmole of palladium acetate (Pd(OAc)$_2$) in 10 ml of acetonitrile at reflux temperature of the solvent for 2 hours. The reaction mixture was analyzed for its components by gas chromatography. Consequently, it was confirmed that the reaction mixture contained 9.28% by area of allyl methyl carbonate and 3.88% by area of allyl acetate in addition to 2-cyclopentenone.

Then, 0.6 mmole of triphenylphosphine (PPh$_3$) was added to the reaction system and the resulting mixture was heated at the reflux temperature of the solvent for 4 hours.

The reaction mixture thus obtained was analyzed for its components as above. Consequently, neither allyl methyl carbonate nor allyl acetate was detected.

The results described above are summarized in Table 1.

Subsequently, the reaction mixture was distilled under conditions of 40 mmHg and 67° C. to give 2-cyclopenenone in 93% yield.

Thus, it was confirmed that the subsequent reaction in the present invention, i.e., the heating after addition of the phosphorus-containing compound, is effective in decomposing and removing the unreacted starting material and the by-product.

EXAMPLE 8

The process of Example 7 is repeated except for adding 0.2 mmole of triphenylphosphine in the previous catalytic reaction, and changing the amount of triphenylphosphine added in the subsequent reaction with heating and the period of the subsequent reaction with heating to 0.4 mmole and 3 hours, respectively. The results of analysis of the reaction mixtures are also shown in Table 1.

Neither the unreacted starting material nor the by-product was detected in the reaction mixture obtained by the subsequent reaction with heating, and 2-cyclopentenone was obtained in 94% yield.

COMPARATIVE EXAMPLE 1

The process of Example 7 was repeated except that in the previous catalytic reaction, the amount of triphenylphosphine added and the reaction time were changed to 0.2 mmole and 3.5 hours, respectively, and that in the subsequent reaction with heating, the amount of triphenylphosphine added and the reaction time were changed to 0.2 mmole and 5 hours, respectively. The results of analysis of the reaction mixtures are shown in Table 1.

It was confirmed that when the amount of the phosphorus-containing compound added is small, allyl acetate remains without decomposition.

REFERENCE EXAMPLE

In a reactor were placed 10 mmoles of allyl acetate, 0.1 mmole of palladium acetate, 0.5 mmole of triphenylphosphine and 10 ml of acetonitrile, and the reaction was carried out at a temperature of 50° C. for 2 hours.

The reaction did not proceed, that is, allyl acetate was not decomposed.

EXAMPLE 9

The procedure of Example 7 was repeated except that 0.4 mmole of pyridine was added and the reaction time was changed to 10 hours in the previous catalytic reaction.

The reaction mixture thus obtained was analyzed for its components as above. Consequently, neither allyl methyl carbonate nor allyl acetate was detected; but it was confirmed that 2-cyclopentenone was obtained in 90% yield.

TABLE 1

| | Previous catalytic reaction | | | | Subsequent reaction | | | |
|---|---|---|---|---|---|---|---|---|
| | pph$_3$/Pd(OAc)$_2$ molar ratio | Reaction time (hr) | Allyl methyl carbonate (%)* | Allyl acetate (%)* | pph$_3$/Pd(OAc)$_2$ molar ratio | Reaction time (hr) | Allyl methyl carbonate (%)* | Allyl acetate (%)* |
| Example 7 | 0 | 2 | 9.28 | 3.88 | 3 | 4 | 0 | 0 |
| Example 8 | 1 | 2 | 11.5 | 2.91 | 2 | 3 | 0 | 0 |
| Comparative Example 1 | 1 | 3.5 | 10.7 | 3.88 | 1 | 5 | 0 | 1.13 |

Note:
*expressed in terms of a percentage by area analyzed by gas chromatography.

The process of the present invention makes it possible to decompose and remove the unreacted starting material and the by-product in a reaction mixture effectively by the subsequent reaction, and therefore it facilitates separation and purification of an $\alpha,\beta$-unsaturated carbonyl compound. This process can provide an $\alpha,\beta$-unsaturated carbonyl compound in high yield and purity.

We claim:

1. A process for producing a 2-cyclopentene-1-one comprising reacting a 1-cyclopentenyl ester and a carbonic ester of formula [III]:

$$R_5-O-\overset{O}{\underset{\|}{C}}-O-\underset{R_6}{\overset{}{C}}-\underset{R_7}{\overset{}{C}}=C\overset{R_8}{\underset{R_9}{\diagdown}}\qquad [III]$$

in the presence of a platinum group metal compound catalyst, wherein $R_5$ is a hydrocarbon residue, and $R_6$, $R_7$, $R_8$ and $R_9$ are independently hydrogen atoms or a hydrocarbon residue.

2. A process as defined in claim 1, wherein the hydrocarbon residue is a $C_1$–$C_8$ alkyl group or $C_2$–$C_8$ alkenyl group.

3. The process according to claim 1, wherein the catalyst is a platinum group metal compound or a catalyst composed of a platinum group metal compound and a ligand.

4. The process according to claim 3, wherein the platinum group metal compound is a salt or a complex of a platinum group metal selected from palladium, platinum, rhodium, iridium or ruthenium.

5. The process according to claim 4, wherein the platinum group metal is palladium.

6. The process according to claim 4, wherein the platinum group metal compound is a zerovalent olefin complex or a divalent organic compound of palladium.

7. The process according to claim 3, wherein the ligand is a monodentate or multidentate electron donor compound having, as a ligan atom, an element of Group V of the periodic table.

8. The process according to claim 7, wherein said element is N, P, As or Sb.

9. The process according to claim 3, wherein the ligand is used in amount of 2.5 moles or less per mole of the metal compound.

10. The process according to claim 1, wherein the catalyst is used in amount selected from 0.01 to 10 moles per 100 moles of the 1-cyclopentenyl ester.

11. The process according to claim 1, wherein the carbonic ester is used in amount of from 0.8 to 5 moles per mole of the 1-cyclopentenyl ester.

12. The process according to claim 1, wherein the carbonic ester is a member of the group consisting of a lower alkyl ester of allyl carbonate, a lower alkyl ester of crotyl carbonate, and a lower alkyl ester of methallyl carbonate.

13. The process according to claim 1, wherein the 1-cyclopentenyl ester is reacted with the carbonic ester at a temperature of 50° C. or more for a period of from 10 minutes to 20 hours.

14. The process according to claim 1, wherein the reaction is carried out in the presence of a diluent.

15. The process according to claim 14, wherein the diluent is one selected from nitriles, sulfoxides, amides, ethers, ketones, esters, alcohols and hydrocarbons.

16. The process according to claim 14, wherein the diluent is an aprotic polar solvent.

17. The process according to claim 14, wherein the diluent is used in such an amount that the concentration of the esters becomes 1 to 50% by weight.

18. The process according to claim 3, wherein said catalyst is composed of a platinum group compound and a ligand.

19. The process according to claim 18, wherein said platinum group metal compound is palladium acetate and said ligand is triphenylphosphine.

20. The process according to claim 4, wherein said platinum group metal compound is palladium acetate.

21. The process according to claim 4, wherein said platinum group metal compound is tris(dibenzlideneacetone)dipalladium.

22. The process of claim 15, wherein said diluent is acetonitrile or dimethyl sulfoxide.

23. A process for producing an $\alpha,\beta$-unsaturated carbonyl compound represented by formula (II):

$$\underset{R_4}{\overset{R_3}{\diagdown}}C=\underset{R_2}{\overset{}{C}}-\overset{O}{\underset{\|}{C}}-R_1 \qquad (II)$$

wherein $R_1$, $R_2$, $R_3$ and $R_4$ are independently hydrogen atoms or hydrocarbon residues, such that $R_1$, $R_2$, $R_3$ and $R_4$ may be linear or may form one or more rings when taken together in arbitrary combinations which comprises subjecting an alkenyl ester represented by formula (I):

$$\underset{R_4}{\overset{R_3}{\diagdown}}CH-\underset{R_2}{\overset{}{C}}=\underset{R_1}{\overset{}{C}}-O=X \qquad (I)$$

wherein $R_1$, $R_2$, $R_3$ and $R_4$ have the same meanings as defined above, and X is an acyl group, and an allyl type carbonic ester to catalytic reaction in the presence of a platinum group metal compound catalyst, adding a phosphorus-containing compound, and heating.

24. The process according to claim 23, wherein the phosphorus-containing compound is a monodentate or multidentate electron donor compound containing phosphorus.

25. The process according to claim 24, wherein the phosphorus-containing compound is a phosphine or a phosphite.

26. The process according to claim 24, wherein the phosphine is a trialkylphosphine or triphenylphosphine.

27. The process according to claim 23, wherein the phosphorus-containing compound is used in such an amount that the total amount of the phosphorus-containing compound used in the catalytic reaction and the reaction with heating is at least 3 moles per mole of the platinum group metal compound catalyst.

28. The process according to claim 23, wherein in the reaction with heating, the reaction temperature is 50° C. or higher and the reaction time is 30 minutes to 10 hours.

29. The process of claim 1, further comprising adding a phosphorus-containing compound followed by heating.

30. The process according to claim 23, wherein $R_1$, $R_2$, $R_3$ and $R_4$, which may be the same or different, are hydrogen atoms, alkyl groups, alkylene groups or aryl groups.

31. The process according to claim 23, wherein the alkenyl ester is a cycloalkenyl ester.

32. The process according to claim 31, wherein the cycloalkene is a 5- to 7-membered ring olefin or a 12-membered ring olefin.

33. The process according to claim 32, wherein the cycloalkene is a 5-membered ring olefin.

34. The process according to claim 23, wherein the allyl type carbonic ester is a lower alkyl ester of allyl carbonate, crotyl carbonate or methallyl carbonate.

35. The process according to claim 23, wherein the allyl type carbonic ester is used in amount of 0.8 to 5 moles per mole of the alkenyl ester.

36. The process according to claim 35, wherein the allyl type carbonic ester is used in amount of 1 to 5 moles per mole of the alkenyl ester.

37. The process according to claim 23, wherein the platinum group metal compound catalyst is a platinum group metal compound or a catalyst composed of a platinum group metal compound and a ligand.

38. The process according to claim 37, wherein the platinum group metal compound is a salt or a complex of a platinum group metal selected from palladium, platinum, rhodium, iridium or ruthenium.

39. The process according to claim 38, wherein the platinum group metal is palladium.

40. The process according to claim 39, wherein the palladium is in the form of a zerovalent olefin complex or a divalent organic compound.

41. The process according to claim 37, wherein the ligand is a monodentate or multidentate electron donor compound having, as a ligand atom, an element of Group V of the periodic table.

42. The process according to claim 41, wherein the ligand atom is one selected from nitrogen, phosphorus, arsenic and antimony.

43. The process according to claim 42, wherein the ligand is a nitrogen-containing compound or a phosphorus-containing compound.

44. The process according to claim 37, wherein the ligand is used in amount of 2.5 moles or less per mole of the platinum group metal compound.

45. The process according to claim 44, wherein the ligand is used in amount of about 2 moles or less per mole of the platinum group metal compound.

46. The process according to claim 23, wherein the platinum group metal compound catalyst is used in amount selected from 0.01 to 10 moles per 100 moles of the alkenyl ester.

47. The process according to claim 23, wherein the catalytic reaction is carried out in the presence of a diluent.

48. The process according to claim 47, wherein the diluent is one selected from nitriles, amides, ethers, ketone, esters, alcohols, sulfoxides and hydrocarbons.

49. The process according to claim 47, wherein the diluent is an aprotic polar solvent.

50. The process according to claim 23, wherein the diluent is used in such an amount that the total concentration of the alkenyl ester and the allyl type carbonyl ester becomes 1 to 50% weight.

51. The process according to claim 23, wherein in the catalytic reaction, the reaction temperature is 50° C. or higher and the reaction time is 10 minutes to 20 hours.

* * * * *